(12) United States Patent
Apajalahti et al.

(10) Patent No.: US 6,271,007 B1
(45) Date of Patent: Aug. 7, 2001

(54) YEAST STRAINS FOR THE PRODUCTION OF XYLITOL

(75) Inventors: Juha Apajalahti, Helsinki; Matti Leisola, Espoo, both of (FI)

(73) Assignee: Xyrofin Oy, Espoo (FI)

( * ) Notice: Subject to any disclaimer, the term of this patent is extended or adjusted under 35 U.S.C. 154(b) by 0 days.

(21) Appl. No.: 08/194,624

(22) Filed: Feb. 7, 1994

Related U.S. Application Data

(63) Continuation of application No. 07/905,870, filed on Jun. 30, 1992, now abandoned.

(30) Foreign Application Priority Data

Jul. 1, 1991 (FI) ....................................................... 913197

(51) Int. Cl.$^7$ ................................ C12P 7/58; C12P 7/02; C12N 1/14; C12N 1/16
(52) U.S. Cl. ....................... 435/137; 435/155; 435/254.1; 435/255.1; 435/255.4; 435/440; 435/441; 435/443
(58) Field of Search ........................... 435/26, 29.1, 155, 435/254, 320.1, 137, 254.1, 255.1, 255.4, 255.5, 255.6, 255.7, 440, 441, 443

(56) References Cited

U.S. PATENT DOCUMENTS

| | | | |
|---|---|---|---|
| 3,586,537 | 6/1971 | Steiner et al. | 127/37 |
| 3,784,408 | 1/1974 | Jaffe et al. | 127/37 |
| 4,008,285 | 2/1977 | Melaja et al. | 260/635 C |
| 4,066,711 | 1/1978 | Melaja et al. | 260/637 R |
| 4,075,406 | 2/1978 | Melaja et al. | 536/1 |
| 4,368,268 * | 1/1983 | Gong | 435/161 |
| 4,511,656 * | 4/1985 | Gong | 435/161 |
| 5,081,026 | 1/1992 | Heikkijä et al. | 435/158 |

FOREIGN PATENT DOCUMENTS

| | | | |
|---|---|---|---|
| 4009676 * | 3/1990 | (DE) . | |
| 0 255 153 A1 | 2/1988 | (EP) | C12N/15/00 |
| 0 321 201 | 6/1989 | (EP) . | |
| 0 450 430 | 3/1991 | (EP) . | |
| 2641545 * | 1/1989 | (FR) . | |
| 60 1 450 95 | 7/1985 | (JP) | C12P/7/18 |
| WO8805467 | 7/1988 | (WO) . | |
| 90/08193 | 7/1990 | (WO) . | |
| 91/10740 | 7/1991 | (WO) . | |
| WO 91/15588 | 10/1991 | (WO) . | |

OTHER PUBLICATIONS

Beutler et al. (1986) Xylitol. In: Methods of Enzymatic Analysis, Third Edition. vol. VI (Metabolites 1: Carbohydrates). Eds. Bergmeyer et al. Verlag Chemie, Deerfield Beach, FL. pp. 484–490. see page 487, Jul. 28, 1986.*

Herskowitz (1987) Functional inactivation of genes by dominant negative mutations. Nature 329(17): 219–222, Sep. 17, 1987.*

Lehninger Biochemistry 2nd edition p 234–235 1979.*

International Search Report for PCT/FI 92/00203 dated Oct. 9, 1992, the corresponding international application.

Dialog File 5 (Biosis) Abstract of Gong, C–S. et al., Quantitative Production of Xylitol From D Xylose By A High Xylitol Producing Yeast Mutant *Candida–Tropicalis* HXP–2.

Dialog File 351 (World Patent Index), English Abstract of JP 60145095.

Gong, C–S et al., "Quantitative production of xylitol from D xylose by a high xylitol producing yeast mutant *Candida––tropicalis* HXP–2," *Biotechnol. Lett* 3(3):130–135 (1981).

Okunev, O.N. et al., (In Russian) "Microbiological transformation of carbohydrates reduction of xylose to xylite by yeast *candida–utilis* strain IBPM–105," *Prikl Biokhim Mikrobiol* 12(3):356–360 (1976).

Barbosa et al., *Journal of Industrial Microbiology* 3:241–251 (1988).

Bianchi et al., *Curr. Genet.* 12:185–192 (1987).

Gatignol et al., *Gene* 91:35–41 (1990).

Hagedorn et al., *Chemical Abstracts* 111:418(1989).

Hagedorn et al., *Curr. Genet.* 16:27–33 (1989).

Hallborn et al., *Bio/Technology* 9:1090–1095 (1991).

Ho et al., *Enzyme Microb. Technol.* 11:417–421 (1989).

James et al., *Applied and Environmental Microbiology* 55 (11): 2871–2876 (1989).

Kötter et al., *Curr. Genet.* 18:493–500 (1990).

Lee et al., *Enzyme Microb. Technol.* 10:81–84 (1988).

Stevis et al., *Applied and Environmental Microbiology* 53(12):2975–2977 (1987).

Stevis et al., *Applied Biochemist and Biotechnology* 20/21:327–334 (1989).

Takuma et al., *Applied Biochemistry and Biotechnology* 28/29:327–340 (1991).

Lehninger *Biochemistry* 2nd Edition p234–p235 1979.*

* cited by examiner

*Primary Examiner*—Ponnathapu Achutamurthy
*Assistant Examiner*—Manjunath N. Rao
(74) *Attorney, Agent, or Firm*—Sterne, Kessler, Goldstein & Fox P.L.L.C.

(57) ABSTRACT

The invention relates to novel yeast strains having a reduced ability to metabolize xylitol. The invention further relates to the use of said strains for the production of xylitol.

60 Claims, No Drawings

US 6,271,007 B1

YEAST STRAINS FOR THE PRODUCTION OF XYLITOL

This application is a continuation of application Ser. No. 07/905,870, filed Jun. 30, 1992 now abandoned.

FIELD OF THE INVENTION

The invention is in the field of metabolic engineering. Specifically the invention relates to a process for producing xylitol using novel yeast strains wherein xylitol metabolism is modified. The invention further relates to the novel yeast strains, and a process for producing such strains.

BACKGROUND OF THE INVENTION

Xylitol is usually prepared by methods in which a xylane-containing material is first hydrolyzed to produce a monosaccharide mixture containing xylose. The xylose is then reduced to xylitol, usually in the presence of a nickel catalyst. A number of processes of this type have been described in the literature in this field. U.S. Pat. Nos. 3,784,408, 4,066,711, 4,075,406, 4,008,285 and 3,586,537 may be mentioned as examples.

However, all of these priori methods are multi-step processes which are relatively costly and have a relatively low efficiency. The greatest problems reside in obtaining an effective and complete separation of xylose from other hydrolysis by-products. The purification is very exacting because the catalysts used in the reduction reaction of xylose are very sensitive. The purity of the final product, on the other hand, is greatly dependent on how well xylitol can be separated from the other products produced in the reduction reaction.

The production of xylitol by means of a biotechnological process is highly attractive if such process is able to provide a very high quality product by a comparatively cost effective method. However, in order to produce xylitol by yeast fermentation for the above purposes, a yeast strain must be found which is non-pathogenic and which meets the requirements set by the food industry. Further, in order to achieve high yields of xylitol with the aid of yeast fermentation, it is essential to employ a yeast which is capable of reducing xylose to xylitol. Preferably, such strain would also be relatively inefficient in the further metabolic conversion of xylitol.

Many yeast strains produce reductase enzymes that catalyze the reduction of sugars to corresponding sugar alcohols. Many yeasts are also capable of reducing xylose to xylitol as an initial step in their xylose metabolism and several yeast strains are able to use xylose as a sole source of carbon and energy. The reaction route or pathway of xylose utilization for the yeast studied is the following: xylitol is synthesized in the first step wherein xylose is reduced to xylitol with the aid of xylose reductase. Xylitol is then metabolized (utilized) by a series of successive steps. First, xylitol is oxidized to xylulose with xylitol dehydrogenase, xylulose is phosphorylated to xylulose-5-phosphate with xylulose kinase (also called xylulokinase), and then part of xylulose-5-phosphate is converted to pyruvate and ethanol via several intermediate steps. The resultant main products and by-products vary depending on the yeast strain and the fermentation conditions. The reactions are not tightly coupled, and consequently some xylitol is always produced in the medium.

Generally, research in this area has focused on attempts to identify yeast strains with an enhanced ability to produce ethanol rather than xylitol. Nevertheless, xylitol production is a relative common feature among xylose-utilizing yeasts. For example, of 44 yeasts in five genera (Candida, Hansentla, Kluyveromyces, Pichia and Pachysolen), 42 produced some xylitol in the culture media (Barbosa, M. F. S., et al., *J. Indust. Microbiol* 3:241–251 (1988) and *Enzyme Microb. Technol.* 10:66–81 (1988)).

It has been suggested to use such strains for the industrial production of xylitol. For example, the industrial use of *Candida tropicalis, Candida guillermondii* and *Candida parapsilosis* has been suggested (PCT applications PCT/FI90/00015 (WO 90/08193), *C. tropicalis*, PCT/FI91/00011 (WO 91/10740), *C. tropicalis, and PCT/FI87/00162* (WO 88/05467), *C. guillermondii*, and French published application 2641545, *C. parapsilosis*). However, all of the above-mentioned Candida strains are potential pathogens and do not meet the requirements of the food industry. Barbosa et al., *J. Industr. Microbiol.* 3:241–251 (1988) describe yeasts screened for the production of xylitol. However, the strains that gave acceptable yields are also all potential pathogens. Therefore, no non-pathogenic strains of yeast that are useful for the production of xylitol have been described that may be utilized in the food industry and/or for production of xylitol on a large scale.

In addition, profitable industrial production of xylitol by the enzymatic conversion of xylose is possible only if the yield is very high. However, no wild yeast strains can achieve this. When different yeast strains were studied in optimum reaction conditions, it was found that certain *Candida tropicalis* strains gave the best yield of xylitol. However, as stated above, the strains of this yeast species are potentially pathogenic and cannot therefore be utilized in the food industry. Species acceptable to the food industry include *Saccharomyces cerevisiae, Candida utilis* and *Kluyveromyces marxianus*. *Saccharomyces cerevisiae* does not normally express enzymes of the xylose pathway although Hallborn, J. et al., *Bio/Technology* 9:1090 (1991) describe the use of the cloned xylose reductase gene from *Pichia stipitis* for construction of *Saccharomyces cerevisiae* strains capable of converting xylose into xylitol with a claimed yield of 95%.

Mutants defective in xylose utilization have been described. Hagedorn, J. et al., *Curr. Genet.* 16:27–33 (1989) discloses that mutants of the yeast *P. stipitis* were identified that were unable to utilize xylose as the sole carbon source and which were deficient in either xylose reductase or xylitol dehydrogenase. James, A. P. et al., *Appl. Environ. Microbiol.* 55:2871–2876 (1989) discloses mutants of the yeast *Pachysolen tannophilus* that are unable to metabolize D-xylose. Stevis, P. E. et al., *Appl. Biochem. Biotechnol.* 20:327–334 (1989), discloses the construction of yeast xyulokinase mutants by recombinant DNA techniques.

The yeasts *Candida uitilis* and *Kluyveromyces marxianus* have the naturally inducible enzymes xylose reductase, xylitol dehydrogenase and xylulose kinase necessary for the decomposition of xylose. Attempts to adjust the chemical and physical environment of the *Candida utilis* and *Kluyveromyces marxianus* yeasts to increase the xylitol yield have, however, been unsuccessful.

SUMMARY OF THE INVENTION

It has now been found that the xylitol metabolism of yeasts can be modified, whereby novel yeast strains are developed producing xylitol at high yields.

Thus, the invention is first directed to novel yeast strains, such yeast strains being capable of xylitol synthesis from xylose, but deficient in one or more enzymes of xylitol metabolism, such that xylitol accumulates in the culture medium and may be recovered therefrom.

The invention is further directed to methods of producing xylitol using such yeast strains.

The invention is further directed to a method of constructing modified yeast strains that are capable of reducing xylose, and are incapable or deficient in their expression of xylitol debydrogenase and/or xylulose kinase activity.

DETAILED DESCRIPTION

The modified yeast strains of the invention can synthesize xylitol from xylose but are deficient in one or more enzymes of xylitol utilization, such that xylitol accumulates in the medium when the modified yeast host is grown on xylose. Thus, in the novel strains, xylose reductase activity is present, but xylitol metabolism is markedly decreased. Consequently, the novel strains are not capable of using xylose as their sole carbon source, even though xylose induces the activity of xylose reductase and thereby the conversion of xylose to xylitol.

The reaction route of xylose reduction is shown below.

Xylose reductase catalyzes the reaction:

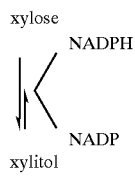

xylose
NADPH
NADP
xylitol

The first enzyme of xylitol utilization, xylitol dehydrogenase, catalyzes the reaction:

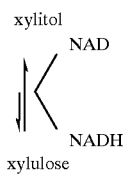

xylitol
NAD
NADH
xylulose

The novel yeast strains produced in accordance with the process of the invention produce xylitol from xylose when another source of carbon and energy for growth and maintenance of the yeast strain has been added to the growth medium. Under culture conditions wherein it is desired to produce xylitol from xylose, the hosts of the invention are genetically incapable of using xylose as a sole carbon source because they are genetically incapable of completely metabolizing xylitol. Since the strains are not capable of metabolizing xylitol, xylitol is accumulated in the growth medium. By "genetically incapable" it is meant that the native yeast DNA has been altered so as to result in a modified yeast host possessing a desired mutation or other genetic alteration that is stably inherited.

Thus, the modified yeast strains of the invention have a high rate of glucose metabolism and xylose reduction, but at the same time a markedly reduced rate of xylitol oxidation into xylulose. The novel strains are thus very effective producers of xylitol. Many yeast strains are known that utilize xylose including, for example, *C. frareli* (such as FTI-20038); *C. guilliermondii* (such as FTI-20037, IZ-803, IZ-1739, IZ-1231, IZ-1322, IZ-1239, IZ-1422, c-138, 17-07, and IZ-1735); *C. intermedia* (such as RJ-245); *C. pseudotropicalis* (such as IZ-431 and 1006); *C. tropicalis* (such as 1004, IZ-1824, IZ-1958, and 53-51); *C. utilis* (such as FTI-20039, 74-64, 1009, EQ2, IZ-1166, IZ-1840 and IZ-1841); *H. anomala* (such as IZ-1420, IZ-229, IZ-781, IZ-1033, RJ-510, IZ-271, IZ-1224, IZ-1260 and FTPTAT-106); *K. fragilis* (such as FTI-20066); *K. marxianus* (such as IZ-1821, 145, IZ-1339, 276, and IZ-619); *Pach. tannophilus* (such as NRRL Y2460); *P. butonii* (such as 68-1111) and *P. stipitis* (such as 79-261). Such yeast may be obtained from a variety of sources, such as, for example, the ATCC, the NRRL, the Agronomic Institute (UNICAMP, Campinas, Brazil); the Foundation for Industrial Technology (FTI, São Paulo, Brazil); the Microbiology Institute (UFRJ, Rio de Janeiro) and the Zymotechnic Institute (ESALQ, Piracicaba). All may be maintained on agar slants or plates as described in the art, for example, in medium containing 10 g/l yeast extract, 20 g/l peptone and 20 g/l D-glucose (Barbosa, M. F. S. et al., *J. Indust. Microbiol.* 3:241–251 (1988)).

When non-pathogenic original strains are used for the production of the novel strains, the resultant mutants also fulfill the special requirements set by the food industry in regard to both quality and yield. Preferably a yeast of the species Candida, Hansenula, Kluyveromyces, Pichia or Pachysolen is used, and especially *Candida utilis* or *Kluyveromyces marxianus*. In a highly preferred embodiment, a strain of *Kluyveromyces marxianus* var. *marxianus* (such as strain CBSC12) or *Kluyveromyces marxianus* var. *bulgaricus* (such as ATCC 16045) or *Kluyveromyces marxianus* var. *lactis* is used. The methods of the invention are applicable for the modification of any yeast wherein it is desired to construct or identify a yeast that is capable of xylitol production but is deficient in one or more enzymes of xylitol utilization. The methods as exemplified below, wherein yeast *Kluyveromyces marxianus* has been employed as a model and starting material, are extendable and applicable to the modification of other yeast species in order to reach the modified yeast hosts of the invention.

*Kluyveromyces marxianus* is a well-known non-pathogenic yeast much used in the food industry. The yeast has been described for instance in *The Yeasts, A Taxonomic Study*, ed. N. J. W. Kreger-van Rij, Elsevier Science Publishers B. V., Amsterdam (1984), wherein synonyms of this yeast have also been stated on page 234. This publication and all other references noted herein are hereby incorporated by reference. The wild strain normally uses glucose as its energy source, but is also capable of metabolizing xylose. Other yeasts fulfilling the special requirements of the food industry, such as certain Candida strains, may also be used for the purposes of the invention.

Preferably, the genes whose expression it is desired to inactivate are those that encode xylitol dehydrogenase and xylulose kinase in the native yeast host. These genes are preferred because they are generally the only route of xylitol metabolism in the host. Therefore, blocking the expression of either (or both) enzymes ultimately blocks xylitol utilization and allows for xylitol accumulation in the medium when the host is grown in the presence of xylose.

The hosts of the invention may be produced by any method that will block xylitol metabolism in a manner as described above. In one embodiment, the process of the invention for producing novel yeast strains is characterized in that the starting strain is cultured in a growth medium containing assimilable sources of carbon and energy, a mutagen treatment and optionally a treatment with an agent interfering with the chromosome division or the microtubulus formation are performed on the culture, the mutants are enriched with an antibiotic, and the yeast strains deficient for xylitol metabolism are screened and harvested.

For example, in this embodiment, mutagenesis by means of a chemical or physical treatment is used. Examples of suitable chemical mutagens are base analogs such as 5'-bromouracil, 2'-aminopurine and 5'-deoxyuridine, deaminating agents such as nitric acid and hydroxylamine, alkylating agents such as ethyl methane sulphonate and nitrosoguanidine, and acridine derivatives such as acriflavine and ethidium bromide. Protocols for the use of these agents are known in the art.

Examples of useful physical mutagenesis methods include, for instance, UV and X-ray irradiation. Protocols for the use of these agents are also known in the art.

Optionally, the yeast may be treated with an agent that interferes with the chromosome division or microtubulus formation in the mitotic cycle. The use of benomyl is as a preferred embodiment. By this treatment, the chromosome with a desired mutation is isolated from the homologous chromosomes present. For haploid yeast strains, this treatment is not needed.

Lastly, yeast modified by a chemical or physical method such as described above are screened for those wherein the desired characteristics of the modified yeast hosts of the invention are present. Enrichment of the auxotrophic cells with an antibiotic, such as nystatin, which kills only cells having active metabolism may be used. The treatment is carried out in the presence of xylose. The culture medium may be assayed directly for the amount of xylose according to methods known in the art to determine the best yeast producers.

Thus, the novel strains may be produced by culturing the starting strain in a suitable growth medium in the conventional manner. A mutagen treatment may be carried out on the resultant culture by chemical or physical methods, for instance using a mutagen producing insertion or deletion, such as acriflavine or proflavine, a mutagen producing point mutation, ethylmetlhane sulphonate, UV irradiation or equivalent. After the optional benomyl treatment, the mutants may be enriched for instance by treatment with nystatin, and finally the yeast strains are screened by cultivating them on xylose-rich and glucose-poor agar. The tiny colonies deficient for xylose metabolism are picked, and pure cultures are formed thereof by conventional techniques. The advantage of using chemical or physical methods to construct a host of the invention is that such methods will easily work with any starting yeast species, and the selection methods (assaying for xylitol production in the medium) are also easily applied to any yeast species. For example, the methods described in the Examples would be expected to provide hosts of the invention not only with the exemplified species, but also with any yeast host that naturally possesses the ability to metabolize xylose.

An alternative procedure for the construction of the hosts of the invention involves the use of recombinant DNA techniques. In a first embodiment, a DNA sequence encoding an enzyme of xylitol metabolism is altered so as to destroy the coding information in such gene, and the altered gene is inserted into the yeast's chromosome in replacement of the native yeast gene, using homologous recombination or gene disruption techniques. Examples of genes that may be targeted in this manner include xylitol dehydrogenase and xylulose kinase. Preferably, xylitol dehydrogenase is targeted for inactivation as this is the first enzyme of xylitol utilization. The inactivation of xylulose kinase is sufficient to ensure high xylitol yield because the equilibrium of the reversible reaction catalyzed by xylitol dehydrogenase is shifted very strongly in favor of xylitol under the conditions which exist inside the yeast cell. If genes encoding both enzymes are targeted for inactivation, then any remaining low level expression of an active form (or fragment) of xylitol dehydrogenase will be compensated for in the host by the lack in xylulose kinase activity.

The methods for the cloning of these genes from yeast are known in the art (see Examples). The genes coding for xylitol dehydrogenase or xylulose kinase may be cloned. for example, by complementation of the corresponding mutations in *Escherichia coli* or yeast. The cloned genes are modified by inserting a DNA sequence selectable in yeast into the coding region of the cloned gene, preferably at a distance of not less than several hundred base pairs from each of the termini of the cloned gene. The selectable marker (preferably a dominant marker conferring an antibiotic resistance phenotype) may either be inserted into a suitable restriction site or manipulated to substitute a fragment of the disrupted gene. The resulting plasmid construction is amplified in bacteria. Suitable restriction enzymes are then used to excise a DNA fragment which has the xylitol dehydrogenase (or xylulose kinase) gene sequences at both its termini and a yeast selectable marker in the middle region. This DNA fragment is subsequently used to transform a yeast strain to antibiotic resistance. Individual transformant clones are checked for the ability to grow on plates containing xylose as the sole carbon source. Successful gene disruption may finally be confirmed by measuring the corresponding enzyme activity in the transformed strain and/or by analyzing the structure of the relevant region of the yeast chromosome by a method known as Southern hybridization.

For example, a suitable modification is the substitution of an internal fragment of the cloned gene with a dominant selection marker for yeast. DNA encoding the bacterial kanamycin resistance gene or bleomycin resistance gene are examples of useful dominant selective markers for yeast. Such constructs may be operably linked to yeast promoter sequences or may utilize the a yeast promoter present at the site of homologous recombination. When the promoter of the gene whose coding sequence is being disrupted is utilized, only those transformants that insert the coding sequence in phase with the desired translational reading frame will be selected. Thus, is it often more convenient to provide a promoter sequence already operably linked to the construct. Any other genes that allows for screening of the cells containing the transforming DNA may be used in place of a gene for antibiotic resistance, for example a gene encoding an essential protein.

Transformation of the yeast cells with a linear DNA fragment which has the partial sequences of the desired target (such as a partial sequence of the xylitol dehydrogenase or xylulose kinase gene) on both DNA termini and the selective marker inside the fragment may be carried out. Such transformation is known to result in a high proportion of the transformants having a deletion mutation in the corresponding gene.

Alternatively, if it is desired to retain the native yeast ability to express xylitol dehydirogenase and/or xylulose kinase, alternative recombinant methods may be used that provide for a selective inhibition of expression of a target enzyme. Such methods include the construction of an antisense RNA or r ibozyme directed against an appropriate desired target, such as the mRNA encoding xylitol dehydrogenase or xylulose kinase. A DNA construct encoding an antisense RNA will possess a DNA sequence that is complementary to the sequence of the target's mRNA and is of a sufficient length to recognize and hybridize to such target mRNA, thus preventing the translation of the target's mRNA in the host cell. A DNA construct encoding an appropriate ribozyme will also possess sufficient DNA sequence to hybridize to the target's mRNA; however, once hybridized to such mRNA, the ribozyme activity catalyzes the cleavage of the mRNA at a site that destroys the ability of such mRNA to support translation of the active protein encoded therein (for example, see EP321,201). The antisense RNA construct or the ribozyme sequence may be operably linked to any appropriate yeast promoter sequence using methods known in the art, and transformed into the yeast hosts in a genetically stable manner using common transformation techniques as also known in the art. Expression of such constructs will be determined by the properties of the operably linked yeast promoter and may be constitutive or inducible or repressible in various growth mediums as desired. The advantage of such constructs is that the native host ability to express a target enzyme is not destroyed. The advantage of making expression of such constructs regulatable in an off/on manner is that the ability of the host to express the target may be highly controlled, expression of the target being prevented only when it is desired to provide for xylitol synthesis.

The efficiency of the novel yeast strains constructed according to the present invention may be further improved by overexpressing xylose reductase cloned from the same yeast or from a different yeast strain. The method for the cloning of the xylose reductase gene from yeast has been described by several authors (Hallborn, J. et al., Bio/Technology 9:1090–1094 (1991); Takuma et al., Appl. Biochem. Biotechnol. 28/29:327–340 (1991); and Strasser et al., DE 4009676 (1991)). The method for using this cloned gene for xylose-xylitol conversion in yeast has also been described (Hallborn, J. et al., Bio/Technology 9:1090–1094 (1991)). The cloned xylose reductase gene may be transferred to a suitable vector capable of propagating in the chosen yeast species. For example, pKD1 based vectors are the preferred vector type for high level expression in *K. marxianus* (Bianchi, M. M. et al., *Curr. Genet.* 12:185–192 (1987)). The xylose reductase gene may be exchanged for another promoter known to function efficiently in the chosen yeast. The mutant yeast strains obtained according to the present invention may then be used as hosts for transformation with the vector(s) providing for the overexpression of the xylose reductase gene.

In all embodiments, and however they are produced, the resultant novel yeast strains of the invention are characterized by a markedly decreased capability of metabolizing xylitol when compared to the native yeast strain. This is due to the fact that one or more of the enzymes of xylitol metabolism, such as xylitol dehydrogenase activity and/or xylulose kinase activity has been modified so that expression of such enzyme either vanishes or decreases (either permanently or in a regulatable manner) as a result of the modification of the yeast. Any carbon source capable of being utilized by the host for energy production may be used to support the growth of the yeast of the invention and to supply the reducing equivlents for the reduction of xylose. This function (supplying the reducing potential) is perhaps more important for the process of the invention than supporting growth of the host cell. For example, glucose is preferably added to the growth medium as an energy source in the amounts known in the art necessary to support growth of the host. Growth conditions of aeration and agitation should be those optimal for the host.

When xylose is provided to the hosts of the invention, the xylose carbon is essentially 'trapped' as xylitol and not available for energy requirements of the host. On account of this property, the novel strains of the invention are highly useful in the production of xylitol. When the mutated strains of the invention are cultured in a xylose-rich nutrient solution, they transform xylose into xylitol with a high efficiency. Their efficiency of conversion and utility for a desired process may be evaluated by using any xylose-containing solutions and hydrolysates, for instance, pure xylose solutions or waste liquor from the wood processing industry, such as spent pulping liquor or cooking liquor or a xylose-rich part thereof. The most effective xylitol producers are harvested and used for the production of xylitol on an industrial scale.

Thus, novel strains metabolizing xylose into xylitol at high yields are obtained as a result of the treatment(s) described above. Since the xylitol metabolism of the strains is defective, the strains do not decompose (degrade or metabolize or utilize) xylitol but the xylitol is accumulated in the growth medium and recovered, for instance, chromatographically, subsequent to the removal of the yeast cells. Any method that is known in the art to purify xylitol from the growth medium may be used (for example, see U.S. Pat. No. 5,081,026, incorporated herein by reference).

The invention will be described in detail by means of the following examples, which are not intended to restrict the invention. It is to be stated in this connection that the process has not been optimized in regard to xylitol production, but in regard to highlighting the differences in the yeast strains.

EXAMPLE 1

Formation of Novel Yeast Strains

*Kluyveromyces marxianus* ATCC 8608 was cultivated on a YDP, DYM or DYM-tartrate medium at pH 6.0 and 30° C. YDP (1,000 ml) contained 10 g yeast extract, 20 g glucose, and 20 g peptone. DYM (1,000 ml) contained 5.0 g $(NH_2)_2SO_4$, 1.0 $KH_2PO_4$, 0.5 g $MgSO_4.7H_2O$, 0.1 g NaCl, and 0.1 g $CaCl_2.2H_2O$. DYM-tartrate contained 7.1 g $Na_2SO_4$, 27.6 g $(NH_4)_2$-tartrate, 6.8 g $KH_2PO_4$, 0.5 g $MgSO_4.7H_2O$, 0.1 g NaCl and 0.1 g $CaCl_2.2H_2O$. DYM and DYM-tartrate were supplemented with a trace element solution (1:1000), a vitamin solution (1:100) and a carbon source; the last two were added after autoclaving. The sugars and sugar alcohols were autoclaved separately in a 20% (wt/vol) solution and the vitamin mixture was sterilized by filtration. The vitamin solution (1000 ml) contained 100 mg L-histidine .HCl.$H_2O$, 0.2 mg biotin, 40 mg calcium pantothenate, 0.2 mg folic acid, 200 mg inositol, 40 mg niacin, 20 mg para-aminobenzoic acid, 40 mg pyridoxine.HCl; 20 mg riboflavin, and 40 mg thiamine.HCl. The trace element mixture (1000 ml) had 500 mg $H_3BO_3$, 40 mg $CuSO_4.5H_2O$, 100 mg KI, 200 mg $FeCl_3.6H_2O$, 400 mg $MnSO_4.H_2O$, 200 mg $Na_2MoO_4.2H_2O$, and 400 mg $ZnSO_4.7H_2O$.

A. Mutagen Treatment a) 100 ml of DYM-glucose (1% wt/vol) with 0.001% (wt/vol) acriflavine was inoculated with *Kluyveromyces marxianus* ATCC 8608 and grown in a shaker for three days. The cells were spun down, washed with 100 ml of sterile 0.9% NaCl and resuspended in 500 ml of fresh YDP. The overnight grown cultures were further transferred into DYM with 2% glucose to be used in benomyl treatment.

b) For ethyl methane sulphonate (EMS) mutagenesis, the cultures grown overnight on YDP were spun down and concentrated to a cell density of $2 \times 10^9$/ml. EMS was added to a final concentration of 30 mg/ml and the suspension was incubated for 2 hours 15 minutes. This treatment killed about 70% of the yeast. 2 ml of the mutagenized cell suspension was diluted to 100 ml of the fresh YDP, grown for two days and then further transferred into DYM with glucose for benomyl treatment.

c) Correspondingly, any chemical or physical mutagenesis method can be used. Dosage is optimized in such a way that the death rate of the microbes is between 10 and 100%. After the treatment, the microbes are transferred to a culturing medium or site wherein the growth is optimal. Thereafter one proceeds to step B.

B. Benomyl Treatment

Cells mutagenized with acriflavine or EMS and subsequently grown in DYM with glucose were harvested by centrifugation and added to a fresh YDP medium to give a cell density of $10^8$/ml. Benomyl (10 mg/ml) was dissolved in dimethylsulfoxide, sterilized by filtration and introduced into the cell suspension to give a final benomyl concentration of 100 $\mu$g/ml. The culture was shaken at 30° C. for two days. The cells were then harvested by centrifugation, washed twice with sterile 0.9% NaCl and resuspended in 5-fold volume of fresh YDP. After 2 days of incubation, the culture was transferred into DYM with glucose to be used in nystatin enrichment. The efficiency of the benomyl treatment was followed by microscopically estimating the frequency of cells with two nuclei. Prior to the microscopic examination, the yeast cells were fixed with acetic acid—formaldehyde—alcohol and stained with HCl-Giemsa as described in detail by Streiblova in (*Yeast, A Practical Approach*, ed. I. Campbell and J. A. Duffus, IRL Press, Oxford (1988)). Correspondingly, some other compound interfering with the chromosome division or the microtubulus formation can be used.

C. Antibiotic Enrichment

Glucose-grown, mutagenized and benomyl treated cells were spun down, washed with a saline solution and resuspended in DYM with no carbon source, to give a cell density of $10^7$/ml. After 8 to 15-hours of starvation, 1 g of xylose per 100 ml of cell suspension was added. Nystatin as suspended in ethanol (1 mg/ml) to kill microorganisms (it cannot be filtered because of its low solubility). The suspension was diluted 1:10 in sterile water, and added to the cultures (10% vol/vol) 15 hours after the xylose addition. To stimulate the killing effect, another pulse of carbon source was added with the nystatin. Incubation in a 30° C. shaker was continued for 2 more hours, after which the cells were harvested and washed with a physiological saline solution. The washed pellet was then resuspended in the original volume of YDP medium. When the living yeast cells had recovered (1 to 3 days), the culture was transferred to DYM with glucose as a sole source of carbon. The death rate in the nystatin treatment was monitored by plate counts (YDP medium) before and after the treatment; more than 99.999% of the cells were killed. In the absence of a carbon source, nystatin killed 0 to 40% of the cells, respectively. Correspondingly, other antibiotic whose killing effect is directed to growing cells only can be used.

D. Site Directed Mutagenesis

The method for cloning the yeast xylitol-dehydrogenase has been described (Kötter, P. et al., *Curr. Genet.* 18:493–500 (1990)) as well as a method for cloning the xylulose kinase gene from different yeast species (Ho, N. W. Y. et al., *Enzyme Microbiol. Technol.* 11:417–421 (1989); Stevis, P. E. et al., *Applied and Environmental Microbiol.* 53:2975–2977 (1987)). A suitable source of dominant selective marker for integrative transformation of yeast is, for example, the plasmid pUT332 (Gatignol, A. et al., *Gene* 91:35–41 (1990)). The construction of a plasmid containing the phleomycin resistance marker inserted into the xylitol dehydrogenase gene may be performed by conventional recombinant DNA methods. A number of transformation methods may be used for introducing the mutated allele of the xylitol-catabolizing gene into the yeast chromosome, for example, transformation of lithium chloride treated yeast cells or transformation of yeast spheroplasts, prepared by lysing yeast cell wall with a suitable enzyme preparation (e.g. Lyticase). For some yeast strains, electroporation is the preferred transformation method. The transformants are selected on the rich medium plates, containing 5–20 micrograms of phleomycin per milliliter, and screened for their ability to synthesize xylitol.

E. Screening of the Mutants

Potential mutants from the nystatin treatment were plated on DYM agar containing 100 mg of glucose and 10 g of xylose per liter. Consequently, the mutants unable to use xylose as their carbon source raised only tiny colonies. Xylose metabolizing yeasts for their part were not carbon limited and grew therefore large colonies. Small colonies were picked and recultivated on YDP agar. The ability of the isolated mutant strains to grow on glucose, xylose and xylulose was determined by first growing the inoculum overnight in YDP liquid medium. A loopful of the culture was then transferred to 25 ml DYM-tartrate medium with various carbon sources (glucose, xylose or xylulose). After 2 or 3 days, the growth of the mutants and that of the wild strain was measured at $A_{600}$. Potentially useful mutants grew readily on glucose, but were unable to use xylose. The strains having this property were taken to further characterization.

The mutant strains selected for further study were cultivated overnight in YDP medium and then transferred to a medium containing 0.5 to 1.0% of glucose as a growth substrate and 1.0 to 5.0% of xylose to serve as a substrate for xylitol production. The cultures were sampled 3 and 7 days after the inoculation for the sugar and sugar alcohol analysis. The samples were passed through 0.2 pm filters to remove cells and precipitates, the filtrates were diluted and analyzed by HPLC. The column used was a strong cation exchanger in $Ca^{2+}$ form (length 25 cm, diameter 8 mm) preceded by Bio Rad Aminex MicroGuard (Richmond, Calif., USA) deashing cartridges. The temperature of the column was 85° C. and it was eluted with $H_2O$ at the rate of 0.6 ml/min. The injection volume was 10 $\mu$l and elution of the compounds was followed by an RI detector. The external standard method was used.

Also *Kluyveromyces marxianus*, var. *marxianus*, for instance, strain CBSC12, var. *bulgaricus*, for instance strain ATCC 16045, and var. *lactis* strains utilizing xylose are useful as starting strains. Correspondingly, any other *K. marxianus* subspecies or substrain growing on xylose can be used for the production of mutants. Firstly, the mutagenization of the yeast strain is optimized with any mutagen. By varying the treatment time or intensity (for instance concentration of chemical mutagen, intensity or distance for UV irradiation), a dose killing more than 10% but less than 100% of the organism is determined. The mutagenized yeasts are grown in the presence of benomyl or some other compound interfering with the microtubulus formation (sublethal concentration). Haploid yeast strains do not need a benomyl treatment or equivalent. The culture is transferred into a fresh growth medium using a carbon source as a growth substrate also enabling the desired mutants to grow. After the growth has started, the cells are transferred for starvation into a medium with no carbon source. Xylose or xylitol and an antibiotic (for instance nystatin) killing the growing cells are added. The concentration of the antibiotic and the treatment time are optimized in advance in such a way that the treatment in the presence of xylose kills about 100% of the unmutagenized cells, but without a carbon source less than 90%. Cells growing on xylose or xylitol are killed, but the desired mutants stay alive. Mutants of the right kind are screened from the living cells, as set forth hereinabove.

The enzymatic activity and xylitol-producing ability of the yeasts were determined in the manner described in Examples 2 to 4.

EXAMPLE 2

Enzymatic Activity of the Novel Yeast Strain

The activities of the most significant enzymes influencing the xylose/xylitol metabolism were determined for the starting strain and the novel yeast strains in the following way:

A strain of Kluyveromyces marxianus was grown overnight in 50 ml of YDP medium to be used as an inoculum for one liter of DYM-tartrate medium with 10 g of xylose and 20 g of glucose as carbon sources and/or inducers. After 2 days of growth the culture was centrifuged and the pellet washed with Sorensen phosphate buffer, pH 7, to remove residual sugar. The cells were resuspended in the same buffer and broken with 5 passages through an X-press at −20° C. DNase type I (50 mg/ml) was added to the melted extract and the mixture was incubated for 1 hour at room temperature. The crude extract obtained was centrifuged at 185000×g for 60 minutes. The enzymes assayed for were soluble and remained in the supernatant. The protein concentration was determined by the Lowry method (J. Biol. Chem. 193:265–275 (1951)).

The xylose reductase activity was determined by following the oxidation of NADPH spectrophotometrically at 340 nm. The reaction mixture contained 700 μl of 50 mM Tris-HCl buffer pH 7.5, 100 μl of 100 mM xylose, 100 μl of a diluted cell extract, and 100 μl of 1 mM NADPH. The reaction was started by adding the reduced nucleotide and followed for two minutes. The initial rate of the reaction was used in determining the specific xylose reductase activity.

The xylitol dehydrogenase activity was determined by following the oxidation of NADH into NAD, which reaction is coupled to the reduction of xylulose to xylitol. The assay was carried out similarly as the xylose reductase assay, except that instead of xylose and NADPH, xylulose and NADH, respectively, were used.

The results obtained have been presented in Table 1.

EXAMPLE 3

Formation of Xylitol With the Novel Yeast Strains

The fermentations were carried out in the manner described in Example 1 in a shaking flask using an aqueous solution of xylose as a source of xylose. Glucose was added as an energy and carbon source to the fermentation broth. The flasks were stirred and effectively aerated.

The results obtained with the starting strain and the new mutated yeast strains are shown in Table 1.

TABLE 1

Xylitol Dehydrogenase Activities Of Strains Of
Kluyveromyces marxianus Cultivated In Shake Flasks

| Strain | Yield of xylitol % | Xylitol dehydrogenase (XDH) nmol/min/mg |
|---|---|---|
| wild | 42 | 330 |
| II-7 | 64 | 76 |
| II-8 | 51 | 39 |
| II-1 | 60 | 255 |
| II-2 | 52 | 185 |
| II-3 | 54 | 289 |
| II-4 | 57 | 329 |
| II-5 | 55 | 315 |
| II-6 | 57 | 352 |

The results obtained with mutants II-1-II-6 are consistant with a mutation in the xylulose kinase gene since these hosts still retain xylitol dehydrogenase activity.

EXAMPLE 4

Formation of Xylitol on a Larger Scale

The ability of the starting strain and the novel yeast strains to produce xylitol in a larger scale process has also been studied. All the chemicals used in the fermentations were of technical grade. Pulping liquor from sulphite processes using two different hardwood species was used as the source of xylose.

The inoculum was cultivated by transferring a colony of yeast to YM broth (100 ml) and cultivating the culture for one day at 30° C. in a shaker (200 rpm). The culture was then transferred to 900 ml NH$_4$-tartrate buffered substrate, pH 6.0, containing 30 g/l of glucose. The inoculum was again grown for one day at 30° C. in a shaker (200 rpm) and then transferred aseptically to a fermenter.

Xylose, xylitol, ethanol and glucose were analyzed by HPLC in the way described in Example 1. The cell mass was determined by dry weight measurement. The fermentation broth was centrifuged, the cell mass was washed with water and dried overnight at 105° C.

The volumetric xylitol production rate was determined in such a way that the time needed for initiation of xylose consumption was ignored. The xylitol yield was calculated as the ratio of xylitol produced to xylose consumed.

The fermentation parameters were as follows: pH 6.0 (25% NaOH), agitation 500 rpm, aeration 4.0 Nl/min. (vvm) and temperature 30° C.

The composition of the growth medium was the following:

| | | |
|---|---|---|
| 240 | g | glucose |
| 250 | g | CSL (Corn Steep Liquor; 45.5% d.s.) |
| 20 | g | (NH$_4$)$_2$SO$_4$ |
| 20 | g | (NH$_4$)$_2$HPO$_4$ |
| 8 | g | KH$_2$PO$_4$ |
| 8 | g | MgSO$_4$ · 7H$_2$O |
| 5 | | liters H$_2$O |
| about 600 g/5 liters xylose (12–13%) | | |

The results are shown in Table 2.

TABLE 2

Ability of Strains of *Kluyveromyces marxianus* To Produce Xylitol On A Larger Scale

| Strain | Glucose Feed g/l/h | Yield % | Xylitol Production rate g/l/h or [g/(g/l/h)] |
|---|---|---|---|
| wild | — | 35.0 | 1.6 [0.060] |
| wild | 0.80 | 36.7 | 1.9 [0.076] |
| II-7 | 0.65 | 68.5 | 2.8 [0.130] |
| II-7 | — | 55.0 | 1.2 [0.094] |
| II-8 | 0.70 | 60.0 | 1.6 [0.09] |
| II-1 | 0.77 | 57.0 | 2.8 [0.09] |
| II-4 | 0.80 | 46.0 | 1.7 [0.07] |
| II-6 | 0.65 | 40.1 | 2.0 [0.10] |

The specific xylitol production rate is shown in parenthesis (g xylitol/g yeast).

The results show that the new yeast strains are excellent producers of xylitol as compared with the starting strain.

Thus, using the process of the invention several mutant strains of *Kluyveromyces marxianus* were obtained which have markedly lower specific activity of xylitol dehydrogenase (XDH), or xylulose kinase, or both, than the prior yeast strains have and which can thus produce more xylitol from xylose than these.

EXAMPLE 5

Construction of Antisense RNA Yeast Strains by Recombinant DNA Methods

The yeast xylitol dehydrogenase gene or that of the xylulose kinase gene from the desired yeast host may be cloned according to methods known in the art for the cloning of these genes (Kötter, P. et al., *Curr. Genet.* 18:493–500 (1990); Ho, N. W. Y. et al., *Enzyme Microbiol. Technol.* 11:417–421 (1989); Stevis, P. E. et al., *Applied and Environmental Microbiol.* 53:2975–2977 (1987)). Alternatively, a cloned gene of xylitol dehydrogenase or xylulose kinase from a first yeast species may be used to identify and clone that gene from a second yeast species if such genes are sufficiently complementary to allow them to cross-hybridize, for example, as demonstrated in preliminary experiments using the cloned DNA from the first yeast host as a probe for hybridization against the restriction digested genomic DNA of the second, desired yeast host, using Southern blot analysis.

From the cloned DNA, a complementary sequence is predicted that will hybridize to the coding sequence for the desired enzyme. This sequence may be synthesized in vitro by chemical means such as described in *Oligonucleotide Synthesis, A Practical Approach*, M. J. Gait, eds., IRL Press, Oxford, 1984. The antisense sequence may be obtained even without knowning the exact coding sequence from any cloned DNA that is directed to a desired gene sequence. Preferably such cloned DNA is in a double-stranded form where one strand is a 'sense' (or coding) strand and one strand the 'antisense' (or non-coding) strand. Antisense constructs may be engineered using techniques as described above and as known in the art by operably linking such double-stranded DNA to a desired yeast promoter in a manner that results transcription of an RNA possessing an antisense (non-coding) sequence. Preferably, the antisense DNA is operably linked to a sequence providing the yeast xylitol dehydrogenase promoter or yeast xylulose kinase promoter so that expression of the antisense RNA occurs under those conditions where expression of the mRNA for the targetted enzyme occurs.

Such antisense constructs may be provided on vectors, transformed into yeast hosts, for example a yeast of the species Candida, Hansenula, Kluyveromyces, Pichia, or Pachysolen, and preferably *Kluyveromyces marxianus* and *Candida utilis*, and most preferably *Klyuveromyces marxianus* var. *marxianus*, *Kluyveromyces marxianus* var. *bulgaricus* and *Klyuveromyces marxianus* var. *lactis*, and grown on an antibiotic, for example, nystatin as previously described. The yeast are grown as previously described and mutant strains selected for further study that are unable to use xylose for growth, or that grow very poorly on xylose, but that are capable of growing on glucose.

EXAMPLE 6

Construction of Ribozyme Yeast Strains by Recombinant DNA Methods

The yeast xylitol dehydrogenase gene or that of the xylulose kinase gene from the desired yeast host may be cloned according to methods known in the art (Kötter, P. et al., *Curr. Genet.* 18:493–500 (1990); Ho, N. W. Y. et al., *Enzyme Microbiol. Technol.* 11:417–421 (1989); Stevis, P. E. et al., *Applied and Environmental Microbiol.* 53:2975–2977 (1987)).

Alternatively, a cloned gene of xylitol dehydrogenase or xylulose kinase from a yeast species may be used to identify and clone that gene from another yeast species if such genes are sufficiently complementary to allow them to cross-hybridize, for example, as demonstrated in preliminary experiments using the cloned DNA from the first yeast host as a probe for hybridization against the restriction digested genomic DNA of the second, desired yeast host, using Southern blot analysis.

A complementary sequence is predicted from the sequence of the cloned DNA that will hybridize to the coding sequence for the desired enzyme as with the antisense RNA construct. This sequence may be synthesized in vitro by chemical means such as described in *Oligonucleotide Synthesis, A Practical Approach*, M. J. Gait, eds., IRL Press, Oxford, 1984. Preferably such DNA is obtained from a cloned DNA in a double-stranded form, where one strand is a 'sense' (or coding) strand and one strand the 'antisense' (or non-coding) strand.

The ribozyme construct of the invention contains the catalytic activity of a ribozyme, such as the Tetrahymena ribozyme, as taught by EP 321,201, and a sufficient length of an antisense RNA sequence directed against the mRNA of a desired target mRNA, such that the antisense RNA construct of the invention will hybridize to the targeted mRNA and position the ribozyme to cleave the MRNA into a form too small to provide an active enzyme.

Ribozyme constructs may be engineered using techniques as described above and as known in the art by operably linking such double-stranded DNA to a desired yeast promoter in a manner that results transcription of the ribozyme-antisense RNA. Preferably, the ribozyme-antisense DNA is operably linked to a sequence providing the yeast xylitol dehydrogenase promoter or yeast xylulose kinase promoter so that expression of the ribozyme-antisense RNA occurs under those conditions where expression of the mnRNA for the targetted enzyme occurs.

Such ribozyme constructs may be provided on vectors, transformed into yeast hosts, for example, a yeast of the species Candida, Hansenula, Kluyveromyces, Pichia, or Pachysolen, and preferably *Kluyveromyces marxianus* and

*Candida utilis*, and most preferably *Kluyveromyces marxianus* var. *marxianus, Kluyveromyces marxianus* var. *bulgaricus* and *Klyuveromyces marxianus* var. *lactis,* and grown on an antibiotic, for example, nystatin as previously described. The yeast are grown as previously described and mutant strains selected for further study that are unable to use xylose for growth, or that grow very poorly on xylose, but that are capable of growing on glucose.

Having now fully described the invention, it will be understood by those with skill in the art that the scope may be performed within a wide and equivalent range of conditions, parameters and the like, without affecting the spirit or scope of the invention or any embodiment thereof.

We claim:

1. A method for the production of xylitol from a non-pathogenic yeast strain, wherein said method comprises:
    (a) selecting a non-pathogenic yeast strain that can synthesize and metabolize xylitol, said yeast strain being, a member of a species selected from the group consisting of Candida, Hansenula, Kluyveromyces, and Pichia and said yeast strain being genetically capable of using xylose as a sole carbon source for growth;
    (b) modifying said yeast strain of part (a), such that metabolism of xylitol is reduced or eliminated and said strain therefore has a genetically reduced ability for using xylose as a sole carbon source for growth after said modifying;
    (c) growing the modified yeast strain of part (b) in xylose-containing medium under conditions in which said xylitol is produced and accumulates in said medium when said strain is growing on said xylose; wherein, said xylitol that is produced is 35%–68.5% of the xylose that is consumed, and
    (d) recovering said xylitol produced in part (c) from said medium.

2. The method of claim 1, wherein as a result of said modifying of part (b) xylitol dehydrogenase activity, or xylulose kinase activity, or both xylitol dehydrogenase and xylulose kinase activity, are reduced or eliminated when compared to said activity in the unmodified yeast strain of part (a).

3. The method of claim 1, wherein said modifying of part (b) comprises the use of a chemical treatment.

4. The method of claim 3, wherein said chemical treatment comprises use of an agent that interferes with chromosome division or microtubule formation.

5. The method of claim 4, wherein said agent is benomyl.

6. The method of claim 3, wherein said chemical treatment comprises the use of a chemical mutagen.

7. The method of claim 6, wherein said chemical mutagen produces an insertion, a deletion or a point mutation in the modified yeast strain's xylitol dehydrogenase gene, xylulose kinase gene or in both said genes.

8. The method of claim 6, wherein said chemical mutagen is selected from the group consisting of acriflavine and ethyl methane sulphonate.

9. The method of claim 8, wherein said chemical mutagen is ethyl methane sulphonate.

10. The method of claim 8, wherein said chemical mutagen is acriflavine.

11. The method of claim 3, wherein said chemical treatment comprises the use of both a chemical mutagen and an agent that interferes with chromosome division or microtubule formation.

12. The method of claim 11, wherein said chemical agent is benomyl.

13. The method of claim 11, wherein said chemical mutagen is selected from the group consisting of acriflavine and ethyl methane sulphonate.

14. The method of claim 12, wherein said chemical mutagen is ethyl methane sulphonate.

15. The method of claim 12, wherein said chemical mutagen is acriflavine.

16. The method of claim 1, wherein said method further comprises an antibiotic enrichment step between parts (b) and (c).

17. The method of claim 16, wherein said antibiotic is nystatin.

18. The method of claim 1, wherein said method further comprises growth and selection in a xylose-rich and glucose-poor growth media between parts (b) and (c).

19. The method of claim 1, wherein said yeast species is Kluyveromyces.

20. The method of claim 19, wherein said Kluyveromyces is *Kluyveromyces marxianus*.

21. The method of claim 20, wherein said *Kluyveromyces marxianus* is selected from the group consisting of *Kluyveromyces marxianus* var. *marxianus, Kluyveromyces marxianus* var. *bulgaricus* and *Kluyveromyces marxianus* var. *lactis*.

22. The method of claim 1, wherein said yeast species is Candida.

23. The method of claim 22, wherein said Candida is *Candida utilis*.

24. The method of claim 1, wherein said xylitol is recovered from the culture medium in part (d) by a process comprising chromatography.

25. The method of claim 1, wherein said xylitol is recovered from the culture medium in part (d) by a process comprising crystallization.

26. A modified non-pathogenic yeast strain, said yeast strain being modified such that metabolism of xylitol is reduced or eliminated and said strain therefore has a genetically reduced ability for using xylose as a sole carbon source as compared to the corresponding unmodified yeast strain, said yeast strain being selected from the group consisting of the species Candida, Hansenula, Kluyveromyces, and Pichia, wherein said modified strain is capable of producing and accumulating xylitol in the growth medium when said modified yeast strain is growing on xylose, and wherein said xylitol that is produced is 35%–68.5% of the xylose that is consumed.

27. The modified yeast strain of claim 26, wherein said yeast strain has a decreased xylitol dehydrogenase activity, or xylulose kinase activity, or both xylitol dehydrogenase and xylulose kinase activity, when compared to said activity in said unmodified yeast strain.

28. A modified non-pathogenic yeast strain, being modified such that metabolism of xylitol is reduced or eliminated and said strain therefore has a genetically reduced ability for using xylose as a sole carbon source as compared to the corresponding unmodified yeast strain, said modified strain being produced by a method comprising:
    (a) selecting a non-pathogenic yeast strain that can synthesize and metabolize xylitol, said yeast strain being selected from the group consisting of the species Candida, Hansenula, Kluyveromyces, and Pichia and said yeast strain being genetically capable of using xylose as a sole carbon source for growth;
    (b) modifying said yeast strain of part (a), such that metabolism of said xylitol is reduced or eliminated and said yeast strain therefore has a genetically reduced ability for using xylose as a sole carbon source for growth after said modifying;

(c) selecting the desired modified yeast strain based upon an increased ability of said modified strain to produce xylitol when compared to the strain of part (a), wherein said modified strain is capable of producing and accumulating xylitol in the growth medium when said modified yeast strain is growing on xylose, and wherein said xylitol that is produced is 35%–68.5% of the xylose that is consumed.

29. The modified yeast strain of claim 28, wherein as a result of said modifying of part (b) xylitol dehydrogenase activity, or xylulose kinase activity, or both xylitol dehydrogenase and xylulose kinase activity, are reduced or eliminated when compared to said activity in the unmodified yeast strain of part (a).

30. The modified yeast strain of claim 28, wherein said modifying of part (b) comprises the use of a chemical treatment.

31. The modified yeast strain of claim 30, wherein said chemical treatment comprises use of an agent that interferes with chromosome division or microtubule formation.

32. The modified yeast strain of claim 31, wherein said agent is benomyl.

33. The modified yeast strain of claim 30, wherein said chemical treatment comprises the use of a chemical mutagen.

34. The modified yeast strain of claim 33, wherein said chemical mutagen produces an insertion, a deletion or a point mutation in the modified yeast strain's xylitol dehydrogenase gene, xylulose kinase gene or in both said genes.

35. The modified yeast strain of claim 33, wherein said chemical mutagen is selected from the group consisting of acriflavine and ethyl methane sulphonate.

36. The modified yeast strain of claim 35, wherein said chemical mutagen is ethyl methane sulphonate.

37. The modified yeast strain of claim 35, wherein said chemical mutagen is acriflavine.

38. The modified yeast strain of claim 30, wherein said chemical treatment comprises the use of both a chemical mutagen and an agent that interferes with chromosome division or microtubule formation.

39. The modified yeast strain of claim 36, wherein said chemical agent is benomyl.

40. The modified yeast strain of claim 36, wherein said chemical mutagen is selected from the group consisting of acriflavine and ethyl methane sulphonate.

41. The modified yeast strain of claim 39, wherein said chemical mutagen is ethyl methane sulphonate.

42. The modified yeast strain of claim 39, wherein said chemical mutagen is acriflavine.

43. The modified yeast strain of claim 28, wherein said method further comprises an antibiotic enrichment step between parts (b) and (c).

44. The modified yeast strain of claim 43, wherein said antibiotic is nystatin.

45. The modified yeast strain of claim 29, wherein said method further comprises growth and selection in a xylose-rich and glucose-poor growth media between parts (b) and (c).

46. The modified yeast strain of any one of claims 27–29, wherein said yeast species is Kluyveromyces.

47. The modified yeast strain of claim 46, wherein said Kluyveromyces is *Kluyveromyces marxianus*.

48. The modified yeast strain of claim 47, wherein said *Kluyveromyces marxianus* is selected from the group consisting of *Kluyveromyces marxianus* var. *marxianus*, *Kluyveromyces marxianus* var. *bulgaricus* and *Kluyveromyces marxianus* var. *lactis*.

49. The modified yeast strain of any one of claims 26–28, wherein said yeast species is Candida.

50. The modified yeast strain of claim 49, wherein said Candida is *Candida utilis*.

51. Culture medium from the culture of a modified non-pathogenic yeast strain in xylose-containing medium, said yeast strain being modified such that metabolism of xylitol is reduced or eliminated and said strain therefore has a genetically reduced ability for using xylose as a sole carbon source as compared to the corresponding unmodified yeast strain, said yeast strain being selected from the group consisting of the species Candida, Hansenula, Kluyveromyces, and Pichia, wherein said modified strain is capable of producing and accumulating xylitol in said medium when said modified yeast strain is growing on xylose, wherein said medium comprises the xylitol that was secreted into said medium during said culture of said modified yeast strain in said medium, and wherein said xylitol that is produced is 35%–68.5% of the xylose that is consumed.

52. A method for the production of xylitol from a non-pathogenic yeast species, wherein said method comprises:

(a) selecting a non-pathogenic yeast strain that can synthesize and metabolize xylitol, wherein said yeast strain selected is from the species Kluyveromyces, said yeast strain being genetically capable of using xylose as a sole carbon source for growth;

(b) modifying said yeast strain of part (a), such that metabolism of xylitol is reduced or eliminated and said strain therefore has a genetically reduced ability for using xylose as a sole carbon source for growth after said modifying;

(c) growing the modified yeast strain of part (b) in xylose-containing medium under conditions in which said xylitol is produced and accumulates in said medium when said strain is growing on said xylose; and, (d) recovering said xylitol produced in part (c) from said medium.

53. The method of claim 52, wherein said yeast strain selected is *Kluyveromyces marxianus*.

54. A modified non-pathogenic yeast strain, said yeast strain being modified such that metabolism of xylitol is reduced or eliminated and said strain therefore has a genetically reduced ability for using xylose as a sole carbon source as compared to the corresponding unmodified yeast strain, wherein said yeast strain is selected from the species Kluyveromyces, and wherein said modified strain is capable of producing and accumulating xylitol in the growth medium when said modified yeast strain is growing on xylose.

55. The method of claim 54, wherein said yeast strain selected is *Kluyveromyces marxianus*.

56. A modified non-pathogenic yeast strain, being modified such that metabolism of xylitol is reduced or eliminated and said strain therefore has a genetically reduced ability for using xylose as a sole carbon source as compared to the corresponding unmodified yeast strain, said modified strain being produced by a method comprising:

(a) selecting a non-pathogenic yeast strain that can synthesize and metabolize xylitol, said yeast strain being selected from the species Kluyveromyces, said yeast strain being genetically capable of using xylose as a sole carbon source for growth;

(b) modifying said yeast strain of part (a), such that metabolism of said xylitol is reduced or eliminated and said yeast strain therefore has a genetically reduced ability for using xylose as a sole carbon source for growth after said modifying;

(c) selecting the desired modified yeast strain based upon an increased ability of said modified strain to produce xylitol when compared to the strain of part (a);

and wherein said modified strain is capable of producing and accumulating xylitol in the growth medium when said modified yeast strain is growing on xylose.

57. The method of claim 56, wherein said yeast strain selected is *Kluyveromyces marxianus*.

58. Culture medium from the culture of a modified non-pathogenic yeast strain in xylose-containing medium, said yeast strain being modified such that metabolism of xylitol is reduced or eliminated and said strain therefore has a genetically reduced ability for using xylose as a sole carbon source as compared to the corresponding unmodified yeast strain, wherein said yeast strain is selected from the species Kluyveromyces, wherein said modified strain is capable of producing and accumulating xylitol in said medium when said modified yeast strain is growing on xylose, and wherein said medium comprises the xylitol that was secreted into said medium during said culture of said modified yeast strain in said medium.

59. The method of claim 58, wherein said yeast strain selected is *Kluyveromyces marxianus*.

60. The method of claims 53, 55, 57, and 59, wherein said *Kluyveromyces marxianus* is selected from the group consisting of *Kluyveromyces marxianus* var. *marxianus*, *Kluyveromyces marxianus* var. *bulgaricus*, and, *Kluyveromyces marxianus* var. *lactis*.

* * * * *